United States Patent [19]

Alvarez

[11] 4,401,655

[45] Aug. 30, 1983

[54] ANTITHROMBOTIC TREATMENT WITH SALTS OF SULFITES AND BISULFITES

[75] Inventor: José A. A. Alvarez, Carpatos, Mexico

[73] Assignee: T & R Chemicals, Inc., Clint, Tex.

[21] Appl. No.: 337,176

[22] Filed: Jan. 5, 1982

Related U.S. Application Data

[63] Continuation-in-part of Ser. No. 271,850, Jun. 16, 1981, abandoned, which is a continuation-in-part of Ser. No. 227,382, Jan. 22, 1981, abandoned, which is a continuation-in-part of Ser. No. 164,845, Jun. 30, 1980, abandoned, which is a continuation-in-part of Ser. No. 75,424, Sep. 14, 1979, abandoned, which is a continuation-in-part of Ser. No. 859,705, Dec. 12, 1977, abandoned.

[51] Int. Cl.$^3$ ............................................. A61K 33/04
[52] U.S. Cl. .................................................... 424/162
[58] Field of Search ......................................... 424/162

[56] References Cited

U.S. PATENT DOCUMENTS 2,367,302  1/1945  Moore .
3,836,639  9/1974  Teler .................................... 424/101
3,906,109  9/1975  Roehm ................................ 424/325

OTHER PUBLICATIONS

Chao, Thrombos, Haemostas (Stuttg), vol. 35, 1976, pp. 717–736.
Shulman, Chem. Abs., vol. 47, 1953, p. 9386.
Gunnison, Fd. Cosmet. Toxicol., vol. 19, 1981, pp. 667–682.
Elias, Abstract of Thromb. Diath Haemorrh, vol. 18, (3–4), 1967, pp. 499–509.
Torda, Abs. of Anaesth. Intens. Care, 1, 293, (1973).
Bourbon, Abs. of J. Eur. Toxicol., vol. 4, No. 3, pp. 205–207, (1971).
Chem. Abs., 9th Coll. Index, p. 37336 CS & vol. 82, Ab. No. 107247f, (1975).
Kikugawa, J. Pharm. Sci., vol. 61, 1972, pp. 1904–1907.
Rost, "Comparative Invst. of the Pharmacol. Effects of Organically Bonded Sulfurous Acids and of Neutral Sodium Sulfite", in Arb. A. D. Kaiserlichen Gesundheitsamte, vol. 21, 1904, p. 312.

Primary Examiner—Anna P. Fagelson
Attorney, Agent, or Firm—Cushman, Darby & Cushman

[57] ABSTRACT

Certain inorganic salts of sulfurous acid display anticoagulant and antithrombotic activity.

19 Claims, No Drawings

ANTITHROMBOTIC TREATMENT WITH SALTS OF SULFITES AND BISULFITES

CROSS-REFERENCE TO RELATED APPLICATIONS

This application is a continuation in part of my earlier filed U.S. patent application Ser. No. 271,850 filed June 15, 1981, and now abandoned, the disclosure and contents of which are entirely incorporated herein by reference which in turn is a continuation in part of my earlier filed U.S. patent application Ser. No. 227,382 filed Jan. 22, 1981, and now abandoned, the disclosure and contents of which are entirely incorporated herein by reference which in turn is a continuation-in-part of my earlier filed U.S. patent application Ser. No. 164,845, filed June 30, 1980, and now abandoned, the disclosure and contents of which are entirely incorporated herein by reference, which in turn is a continuation-in-part of my copending U.S. patent application Ser. No. 075,424, filed Sept. 14, 1979, and now abandoned, the disclosure and contents of which are entirely incorporated herein by reference, which in turn is a continuation-in-part of my earlier filed U.S. patent application Ser. No. 859,705, filed Dec. 12, 1977, and now abandoned, the disclosure and contents of which are entirely incorporated herein by reference.

BACKGROUND OF THE INVENTION

Sodium bisulfite (usually shown by formula to be $NaHSO_3$) has heretofore been used for many commercial purposes, such as a preservative for prevention of the deterioration of liquids such as food stuffs and pharmaceutical solids, and has been used medically externally for parasitic skin diseases and internally as a gastrointestinal antiseptic.

The solid sodium bisulfite of commerce reportedly consist chiefly of sodium metabisulfite, $Na_2S_2O_5$, and sodium bisulfite, and, for purposes of this invention, such is believed to possess the same properties as (and to be equivalent to) sodium bisulfite when dissolved in an aqueous solution.

Anticoagulants and antithrombotics are a group of compounds with diversified pharmacologic actions, used in a variety of chemical thrombotic disorders. Thrombotic disorders are generally divided into venous thromboses and arterial occlusive disorders. Venous thrombsis of the lower extremities is important because it can cause pulmonary embolism which may be fatal. Heparin and warfarin are commonly used in clinical medicine for prevention and treatment of deep venous thrombosis and pulmonary embolism. Their pharmacological actions are in the inhibition of blood coagulation activity (i.e., heparin) or of synthesis of coagulation factors (i.e., warfarin). Platelets play an important part in arterial thrombosis. Drugs that inhibit platelet aggregation are generally regarded as being potentially useful for prophylactic therapy of arterial thrombotic disorders, including, for example, stroke, myocardial infarction and peripheral vascular disease. Despite the availability of many agents which possess anti-platelet aggregating properties, only a few are currently under clinical trials (for example, aspirin, dipyridamole, sulfinpyrazone). None of these agents exhibit unequivocal efficacy. Compounds with more specific pharmacological action are urgently sought in order to provide better medical care for patients with these serious disorders.

An anti-platelet aggregatory agent is a substance which inhibits platelet aggregation.

An antithrombotic agent is a substance which inhibits formation or development of a thrombus (or thrombosis). For present patent purposes, it will be understood that the term "thrombus" or equivalent includes the subject matter of the term "embolus" unless otherwise specifically indicated. In general, an antithrombotic agent may display in the presence of mammalian blood or appropriately prepared plasma anticoagulant activity and/or anti-platelet aggregatory activity.

BRIEF SUMMARY OF THE INVENTION

There has now been discovered a class of inorganic agents the members of which, when introduced as by ingestion, injection, absorption, or otherwise introduced into a mammal (including man), produce amelioration of a thrombotic condition in mammals and man when used in an antithrombotically effective amount as taught herein.

The active antithrombotic agents of the present invention are inorganic salts of sulfurous acid which display anticoagulant and antithrombotic activity. Thus, these agents are selected from existing compounds in the group consisting of pharmaceutically acceptable alkali metals, alkaline earth metals and ammonium salts of sulfites and bisulfites (including metabisulfites) and mixtures thereof. Alkali metal (particularly sodium and potassium) bisulfite are presently most preferred active agent also, because of toxicological considerations, the calcium, magnesium, and ammonium compounds are also preferred. By the term "pharmaceutically acceptable" as used herein reference is had to those alkali metals and alkaline earth metals which are commonly and normally found in appreciable quantities as ions in the blood of mammals including man and which are regarded as being non-toxic for pharmaceutical purposes. Preferably, such metals which are preferred for use in this invention have atomic weights between about 23 (e.g. sodium) and about 40 (e.g. calcium).

Naturally, an active antithrombotic agent of this invention is used, if at all in a mammal, at a pharmaceutically effective dose rate—that is, at a dose rate which is below the level of toxicity or the production of undesired side effects. Because of biological complexities, the complete biological effects of the active agents of this invention are not now known.

Antithrombotic agents of this invention are used in both arterial thrombosis and venous thrombosis. Examples of clinical thrombotic conditions include stroke (as a cerebral vascular thrombosis), myocardial infarction (coronary artery disease), peripheral vascular disease, cardiac valve replacement, deep veins thrombosis, pulmonary embolism, and the like.

The mechanisms by which the active agents function is presently unknown; however, an inhibition of platelet aggregation and a prolongation of normal blood coagulation time appear to be associated with use thereof in the manner taught by the present invention.

In one aspect, the present invention is directed to the use of certain inorganic bisulfite and sulfite compounds as antithrombotic agents in human medicine.

In another aspect, the present invention is directed to a method for control of, and/or prevention of, an embolus or a thrombus in many by oral ingestion and/or injection of a pharmaceutically effective amount of sodium bisulfite and/or other compound(s) within the scope of active agents of this invention.

In another aspect, the present invention provides symptomatic and objective improvement in a thrombotic (including cardiovascular) disease condition, such as, for example, abnormal coagulation, or an intravascular thrombosis, in man. By the term "symptomatic improvement" as used herein, reference is had to an improvement in a patient's subjective symptoms (e.g., as reported by the patient). By the term "objective improvement", as used herein, reference is had to a measureable and objective change in a patient's condition.

Other and further aspects, objects, purposes, advantages, aims, utilities, features and the like will be apparent to those skilled in the art from a reading of the present specification.

DETAILED DESCRIPTION

More particularly, this invention concerns a process of treating a human or other mammal wherein there is introduced orally and/or by injection into such mammal a pharmaceutically effective amount of active agent as an antithrombotic.

Sulfite and/or bisulfite anions do not normally occur in human tissues or blood, so far as is known.

In medicine, for example, arterial thrombosis is diagnosable by clinical manifestations, by arteriography, and recently, by an Indium 111 platelet labeling technique (see, for example, the article entitled "Differential Effects of Two Doses of Aspirin on Platelet-Vessel Wall Interaction in Vivo" by K. K. Wu et al. being published in the Journal of Clinical Investigation, August, 1981.

Also in medicine, for example, it is detectable from patient conditions symptomatically perceivable by a skilled medical practitioner and well known to the art of medicine. Objectively, several methods including venography, impedance plethysmography, doppler ultrasound and the $I^{125}$-fibrinogen test; (see, for example, the article by Kakkar, "Archives of Surgery", 104, page 152 (1972) and Kelton, J. G. et al., Journal of Clinical Investigation, Vol. 62, pgs. 892–895, (1978).

The present invention does not contemplate feeding a normal patient (that is, one not suffering from a thrombotic condition) an active agent of this invention at a pharmaceutically effective dosage as indicated herein.

By the term "thrombotic condition" as used herein, reference is had both to:

(a) an existing thrombus (including an embolus); and/or (b) an incipient thrombus (including an incipient embolus).

An "incipient thrombus" or "incipient thrombotic condition", as such a term is used herein, can exist in a patient who has a predisposed condition for development of a thrombotic condition. For examples, in a diabetes mellitus, hyperlipidemia, and the like are conditions which predispose a patient to arterial thrombosis. On the other hand surgery, trauma, and bed rest and the like for a few examples, predispose a patient to venous thrombosis.

Those skilled in the practice of medicine routinely determine the presence of a thrombotic condition (including on actual thrombus in a patient). Such a condition is determined for the present invention preferably by state of the art techniques. Such determination techniques are known to the prior art and do not as such constitute a part of the present invention.

Preferably, to practice this invention in vivo, one introduces into blood of a mammal, such as a human, the equivalent of from about 1 to 100 milligrams per kilogram of mammal body weight (including human) per day, though larger and smaller dose rates may be employed, if desired, within the spirit and scope of this invention. The exact amount of dose in any given case is selected to be sufficient and appropriate for achieving a desired antithrombotic effect.

In general, to initiate practice of the present invention such an introduction may be commenced at a dosage rate within a range as above indicated as soon as a thrombotic condition (or a thrombus) is found to exist in a patient.

Thus, and for example, in a preferred practice of this invention, as a first step, a determination is made that a patient suffers from a thrombotic condition. Then, one starts orally feeding and/or injecting such patient with at least one active agent of the present invention at an effective dose rate in the range above indicated. Presently, the more preferred dose rate is believed to be from about 4 to 50 mg/kg per day. Preferably, at least two or three spaced doses per day are employable, each such dose being conveniently administered around meal time. Any convenient dose arrangements can be employed.

Not uncommonly, it is desirable or necessary to start treatment immediately upon the discovery of a patient's thrombotic condition to avoid damage, injury, or perhaps even death of the patient, as from an embolus. If oral administration is not convient or rapid enough for a situation, the active agent can be directly introduced by injection into a patient, if desired, such as intravenously, intraperitoneally, intramuscularly, subcutaneously, or the like. Absorption through a membrane, such as a dermal layer may also be used, as when an active agent is dissolved in an appropriate solvent. Suppositories can be used to achieve absorption if dissolved in an appropriate solvent. When an active agent is so directly introduced, it is preferably dissolved in an aqueous medium wherein the total amount of active agent introduced into such medium is preferably within the range from about 1 to 11 weight percent (based on the total solution weight). Distilled water is a presently preferred solvent for such a medium. If desired, conventional (standardized) aqueous media can be used as vehicles for such introduction; for example, standard saline solutions can be used as vehicles.

A present preference is to withdraw samples of blood from a patient undergoing treatment and to measure platelet aggregation. One method is described in the paper by Born, G., Nature 194, pp. 927–929 (1962) may be used for this purpose if desired.

After administration has started, the dose rate is preferably adjusted to a value which is sufficient to disrupt platelet function and/or coagulation factors and thereby achieve a desired antithrombotic effect.

An active agent of this invention, for example, is characteristically capable of inhibiting platelet aggregation both in vitro and in vivo. Also such an active agent is characteristically capable of lengthening both PT (prothrombin time) and PTT (blood partial thromboplastin time) in vitro. Dose rate of active agent is presently believed to be directly proportional to resulting effects upon blood factors, such as under this preferred procedure, use of an active agent at a suitable dose for an individual patient ameliorates that patient's thrombotic condition.

Selected blood parameters of a patient are preferably determined before dosing with active agent is started, as when time permits. Preferably, a dose rate adjustment is accomplishable after administration of an active agent has commenced and is continuing. The amount of adjustment (or incremental change in dosage) is determinable by comparing a patient's measured values during administration of active agent to desired values (such as the patient's own starting corresponding values, normal species e.g. human, values, or the like). Inhibition of platelet aggregation can be used for measurements. Then, the deviation, if any, from the patient's such measured values is compared to such desired values (the patient's starting values, normal species values, or the like). Then, a change in dose rate may be undertaken to correct for any deviation so determined.

For instance, in humans normal values for platelet aggregation are dependent upon the particular agent used for stimulation. For example, when adenosine diphosphate (ADP) at 3 millimolar concentration is employed, platelet aggregation values fall typically in the range between 50% to 100% of light transmission. Other stimulation agents include collagen, epinephrine, arachidonic acid, and the like.

Also, for instance, in humans, normal PT values are believed to fall in the range from about 11 to 13 seconds while normal PTT values are believed to fall in the range from about 25 to 41 seconds. If PT values and/or PTT values could be measured in a given patient, as for purposes of achieving a desired antithrombotic effectiveness, it is currently estimated that a lengthening of PTT value of from about 1.5 to 2 times a PTT value in such normal range in a given starting patient is appropriate (suitable) for antithrombotic effectiveness, which is equal to a lengthened PTT value for a given patient of from about 45 to 60 seconds; such an estimate is consistent, for example, with the lengthened PTT values achieved in the human use of heparin, a prior art agent sometimes previously employed as an antithrombotic agent. Similarly, it is currently estimated that a lengthening of PT value of about two times a PT value in such normal range in a given starting patient is appropriate (suitable) for antithrombotic effectiveness, which is equal to a lengthened PT value for a given patient of from about 22 to 26 seconds; such an estimate is consistent, for example, with the lengthened PT values achieved in the human use of coumadin (warfarin), a prior art agent sometimes previously employed as an antithrombotic agent. The active agents of the present invention, contrary to such prior art agents, appear to effect in vitro both PT and PTT values in a given patient, surprisingly. The mechanism by which the present active agents work is apparently substantially different from, and not comparable to, the prior art agents. Study and evaluation of the active agents of this invention continues.

Contrary to such prior agents (like heparin and coumadin) the active agents of the present invention appear to affect both blood coagulation factors and platelet aggregation. Conveniently and preferably, measurements of blood factors are carried out periodically, such as every 3 to 7 days, on a patient undergoing treatment under the practice of this invention.

An active agent can be orally consumed in the form of a capsule, a tablet, or the like, or in the form of a solution (e.g. aqueous). Also, an active agent can be injected in the form of an aqueous solution.

A particularly presently preferred antithrombotic field of use is in post operative patient treatment, as when arteries or deep veins may be involved in, or threatened by, a thrombotic condition.

By way of explanation, as those familiar with mammalian anatomy appreciate, the venous system in the lower extremities consists of superficial and deep veins. Because of the manner in which the deep veins interconnect and supply blood to the heart and lungs, a thrombus occurring in the deep veins, but not in the superficial veins, can become the source of a blood clot which is moved through the veins and becomes lodged in the lungs, resulting in a pulmonary embolus, which can have obvious catastrophic effects (including causing death). Examples of deep veins include the iliac, the femoral, the popliteal calf veins, and the like. The prevention of pulmonary emboli following surgery affecting the deep veins in the lower extremities is a significant medical problem. One solution to this problem is to prevent thrombi from occuring and/or developing in deep veins. To achieve this solution, active agents of this invention appear to be well suited. Thus, in one such mode of this invention, one may achieve a symptomatic and objective improvement of a deep vein thrombotic complication in a patient during post-operative care following surgery, inhibiting intravascular thrombus formation (including embolism).

In one preferred mode of using this invention, an aqueous solution of from about 1 to 15 percent by weight of an active agent of this invention, preferably sodium bisulfite, is prepared. Then, such solution is orally consumed by a human or injected at the total (or accumulated) dose rate ranging from about 1.0 to 50 mg per each kg of body weight per day, more preferably in the form of at least two spaced doses per day, and still more preferably in the form of at least three spaced doses per day, such a dose being preferably taken around meal time. Solid or encapsulated active agents may be orally consumed alternatively.

Because of the tendency for alkali metal bisulfites to undergo oxidation when in aqueous solution, it is presently common and even preferred in practicing this invention to employ a solution which comprises on a 100 percent by weight total solution basis:

(a) from about 1 to 10 percent by weight of dissolved inorganic solids, and (b) the balance up to 100 percent by weight of any given solution being water.

In such a solution, such dissolved inorganic solids can comprise on a calculated 100 percent by weight dry basis:

(a) at least about 50 and more preferably at least about 90 percent by weight sodium bisulfite, and (b) the balance up to 100 percent by weight thereof being inorganic compounds produced or producible by the oxidation of sodium bisulfite.

The water used in such a solution is preferably purified (e.g., filtered, deionized, distilled, or the like). After preparation, such a solution is preferably stored in a closed container to reduce oxidation.

Such an aqueous solution can be directly used in accordance with the teachings of this invention, in which such a solution can be dispensed dropwise, or such a solution can be encapsulated, or the like, and used as measured dosage units, as desired. For example, an aqueous solution containing 5 weight percent of sodium bisulfite can be injected into a patient or it can be directly consumed by a patient as drops (e.g., from about 5 to 9 drops per meal for each of the two or three meals eaten by such patient per day, depending upon an individual patient's body weight, or the like).

Symptomatic improvement in varicose veins and in hemorrhoids has been observed when using an active agent such as sodium bisulfite at a dose rate of from about 1 to 20 mg/kg of body weight per day.

A lengthened blood coagulation time in a human using sodium bisulfite has been observed by the inventor when given at a dose rate ranging from about 4 to 50 mg/kg of body weight, per day, though it is believed that larger and/or smaller doses can be used without departing from the spirit and scope of the present discovery.

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF ACTIVE AGENTS

EXAMPLE A

A solution of sodium bisulfite is prepared by dissolving pharmaceutical grade (U.S.P. Grade) powdered sodium bisulfite (sodium metabisulfite) in distilled water at room temperature to form a 1 percent by weight aqueous solution.

This solution is then placed into a series of plastic squeeze bottles, each with a volumetric capacity of about 50-52 ml. Each bottle is provided with a cap permitting dropwise dispensing of solution from such bottle at an estimate rate of 15 drops per ml.

EXAMPLE B

A solution of sodium bisulfite is prepared by dissolving pharmaceutical grade (U.S.P. Grade) powdered sodium bisulfite (sodium metabisulfite) in distilled water at room temperature to form a 2 percent by weight aqueous solution.

This solution is then placed into a series of squeeze bottles, each with a volumetric capacity of about 50-52 ml. Each bottle is provided with a cap permitting dropwise dispensing of solution from such bottle at an estimated rate of 15 drops per ml.

EXAMPLE C

A solution of sodium bisulfite is pharmaceutical grade (U.S.P. Grade) powdered sodium bisulfite (sodium metabisulfite) in distilled water at room temperature to form a 2.5 percent by weight aqueous solution.

This solution is then placed into a series of plastic squeeze bottles, each with a volumetric capacity of about 50-52 ml. Each bottle is provided with a cap permitting dropwise dispensing of solution from such bottle at a rate estimated to be 15 drops per ml.

EXAMPLE D

A solution of sodium bisulfite is prepared by dissolving pharmaceutical grade (U.S.P. Grade) powdered sodium bisulfite to form a 5 percent by weight aqueous solution.

This solution is then placed into a series of plastic squeeze bottles, each with a volumetric capacity of about 50-52 ml. Each bottle is provided with a cap permitting dropwise dispensing of solution from such bottle at an estimated rate of 15 drops per ml.

EXAMPLE E

The procedure of Example D above is repeated except that a 7½ percent by weight solution of sodium bisulfite is prepared.

EXAMPLE F

The procedure of Example D is repeated except that a 10 percent by weigh solution of potassium metabisulfite is prepared.

EXAMPLE G

Baker analytical grade sodium bisulfite is placed into gelatin capsules so that each capsule contains 75 mg of sodium bisulfite.

EXAMPLE H

Baker analytical grade sodium bisulfite is placed into gelatin capsules so that each capsule contains 50 mg of sodium bisufite.

PRACTICE OF THE INVENTION

EXAMPLE I

That sodium bisulfite is an antiplatelet aggregatory agent is shown by using a platelet aggregometer based on the technique of Born (above cited). It is found that this material at a concentration of 1 millimolet (mM) abolishes platelet aggregation in human platelet rich plasma induced by optimal concentrations of ADP, collagen, epinephrine, and arachidonic acid.

A similar effect is observed in rabbit platelet rich plasma except that slightly higher concentrations of this material are required to achieve equivalent effect.

This indicates that this material does have significant in vitro inhibitory effect on platelet aggregation. Based on these results, it appears that this material would be suitable for use as an antithrombotic agent.

EXAMPLE II

Sodium bisulfite is evaluated under in vivo conditions by an indium 111 platelet labeling technique in rabbits (see the Wu et al. article above cited). The material was administered by intraveneous injection (72.80 milligram per kilogram of animal body weight).

TABLE I

|  | Platelet Accumulation | | | |
|---|---|---|---|---|
|  | I. at damaged vessel wall | | II. normal at vessel wall | |
| Rabbit | cpm/gm* | %** | cpm/gm | % |
| A | 133,986 | 0.11 | 98,611 | 0.08 |
| B | 146,630 | 0.15 | 83,066 | 0.08 |
| Control (means ± S.D. of 10 animals) | 1,167,820 ± 21,310 | 0.44 ± 0.08 | 72,140 ± 39,040 | 0.03 ± 0.02 |

*Cunt per minute per gram dry weight of tissue.
**% = percentage of injected radioactivity per gram dry weight of tissue.

The findings indicate that the active agent reduces accumulation of platelet thrombus at the damaged vessel wall by 70%.

EXAMPLE III

The alkali metabisulfites, sodium and potassium, and ammonium bisulfite are found to prolong PT and PTT in a dose-related fashion. When aded to human, rabbit, and rat plasma in vitro, both agents significantly prolong PT and PTT at a concentration of 0.5 mg/ml concentration of agent and the effects are found to be dose-related. The results are shown in Table II below.

The evaluation procedure used is described in a standard textbook, entitled "Human Blood Coagulation, Haemostatis and Thrombosis", edited by Rosemary Biggs, published by Blackwell Scientific Publications, Oxford, England (2nd edition), pages 670–705, 1976.

EXAMPLE IV

The effect of U.S.P. grade sodium bisulfite on blood coagulation factors is evaluated by standard procedures (Biggs) and the results are shown in Table III below.

The work is replicated using chemical grade sodium bisulfite and the results are shown in Table IV below.

These results indicate that sodium bisulfite at a concentration of 0.5 mg per ml has a significant inhibitory effect on Factors IX, X, XI, XII, and VII. Factor II and Factor VIII are mildly affected by this agent. The effect is directly proportional to dose. At 5 mg/ml the coagulation of human plasma is completely disrupted.

When this procedure is repeated using rabbit and also rat plasma, similar results were observed except that blood coagulation factors in these species are not as sensitive as respects their response to this agent.

When this procedure is repeated using human plasma, but employing potassium bisulfite and ammonium bisulfite, similar results are obtained.

TABLE II
ACTIVITIES OF VARIOUS ACTIVE AGENTS

| Example Designation | Active Agent (0.5 mg/ml) | PT (seconds) Exp. 1 C | PT (seconds) Exp. 1 A | PT (seconds) Exp. 2 C | PT (seconds) Exp. 2 A | PTT (seconds) Exp. 1 C | PTT (seconds) Exp. 1 A | PTT (seconds) Exp. 2 C | PTT (seconds) Exp. 2 A |
|---|---|---|---|---|---|---|---|---|---|
| TEST SEQUENCE A | | | | | | | | | |
| 7 | Sodium Metabisulfite | 13.4 | 18.5 | 14.1 | 21.9 | 42.1 | 76.9 | 50.5 | 80.3 |
| 7.2 | Sodium Sulfite | 13.4 | 16.2 | 14.1 | 17.7 | 42.1 | 66.1 | 50.5 | 80.7 |
| 7.3 | Ammonium Sulfite | 13.0 | 14.7 | 14.1 | 16.9 | 44.7 | 56.5 | 50.5 | 65.2 |
| 7.4 | Sodium Bisulfite | 13.9 | 22.1 | 14.1 | 23.2 | 53.8 | 128.2 | 50.5 | 121.9 |
| 7.5 | Potassium Metabisulfite | 13.9 | 18.3 | 14.1 | 22.0 | 53.8 | 77.6 | 50.5 | 111.3 |
| TEST SEQUENCE B | | | | | | | | | |
| 7.6 | Sodium Sulfite | 13.1 | 16.8 | 13.5 | 17.7 | 44.0 | 74.8 | 44.5 | 82.1 |
| 7.7 | Sodium Bisulfite | 13.5 | 25.5 | — | — | 44.0 | 128.2 | 44.5 | 162.6 |
| 7.8 | Potassium Metabisulfite | 13.5 | 20.4 | — | — | 44.0 | 91.6 | 44.5 | 105.2 |

C = Control
A = Active Agent

TABLE III
EFFECTS OF SOLUTION D ON COAGULATION IN VITRO

| Coagulation Parameters* | Control | Sodium Bisulfite Concentration (mg/ml) 0.01 | 0.05 | 0.1 | 0.5 | 1.0 | 5.0 |
|---|---|---|---|---|---|---|---|
| PT (sec)$^S$ | 34.67 | 33.37 | 34.00 | 34.85 | 42.73 | 85.33 | >150 |
| PTT (sec)$^S$ | 12.20 | 12.33 | 12.43 | 12.85 | 15.43 | 22.63 | >150 |
| TT (sec)$^S$ | 12.00 | 12.07 | 12.10 | 12.00 | 13.97 | 16.08 | 34.3 |
| FIBRINOGEN (mg %) | 218 | 222 | 228 | 217 | 190 | 185 | 130 |
| PROTHROMBIN (%) | 87 | 79 | 80 | 72 | 40 | 26 | 5 |
| FACTOR V (%) | 75 | 74 | 72 | 80 | 70 | 60 | 54 |
| F VII (%) | 73 | 67 | 57 | 51 | 23 | 8 | 1 |
| F VIII (%) | 57 | 62 | 68 | 55 | 58 | 29 | 11 |
| V IX (%) | 66 | 60 | 52 | 56 | 4 | 3 | <1 |
| F X (%) | 78 | 73 | 68 | 66 | 31 | 11 | 3 |
| F XI (%) | 117 | 98 | 81 | 58 | 27 | 4 | <1 |
| F XII (%) | 86 | 94 | 87 | 79 | 17 | 3 | <1 |

*values represent mean of 5 determinations in duplicate
abbreviations: PT: Prothrombin Time; PTT: Partial Thromboplastin Time; TT: Thrombin Time
Methods for PT, PTT, TT and FACTOR assay are standard

TABLE IV
EFFECTS OF CHEMICAL GRADE SODIUM BISULFITE ON BLOOD COAGULATION IN VITRO

| Coagulation Parameters* | Control | Sodium Bisulfite Concentration (mg/ml) 0.01 | 0.05 | 0.1 | 0.5 | 1.0 | 5.0 |
|---|---|---|---|---|---|---|---|
| PTT (sec) | 34.67 | 32.80 | 33.77 | 34.40 | 44.87 | 78.46 | >150 |
| PT (sec) | 12.20 | 12.30 | 12.47 | 12.90 | 16.10 | 22.38 | >150 |
| TT (sec) | 12.00 | 12.20 | 12.30 | 12.15 | 14.53 | 16.23 | 35.5 |
| FIBRINOGEN (mg %) | 218 | 228 | 245 | 218 | 182 | 184 | 119 |
| PROTHROMBIN (%) | 87 | 88 | 82 | 75 | 34 | 25 | 8 |
| FACTOR V | 75 | 70 | 68 | 68 | 64 | 66 | 60 |
| F VII | 73 | 62 | 63 | 53 | 17 | 7 | 2 |
| F VIII | 57 | 58 | 55 | 56 | 55 | 31 | 13 |
| F IX | 66 | 49 | 44 | 40 | 5 | 1 | <1 |
| F X | 78 | 80 | 69 | 66 | 22 | 6 | 4 |
| F XI | 117 | 83 | 82 | 55 | 24 | 2 | <1 |
| F XII | 86 | 104 | 102 | 75 | 25 | 9 | <1 |

*values represent mean of 5 determinations in duplicate
abbreviations: PT: Prothrombin Time; PTT: Partial Thromboplastin Time; TT: Thrombin Time
Methods for PT, PTT, TT and FACTOR assay are standard

EXAMPLE V

The anti venous thrombotic effect of sodium bisulfite is evaluated in rabbits by using $I^{125}$ fibrinogen technique as described in the article in: "Archives of Surgery", Vol. 104, pg. 152 (1972).

The rabbit was continuously infused with aqueous sodium bisulfite solution at the rate of 0.460 mg/kg/hr (1.058 gram per hour for an animal body weight 2.3 kg) for a time of about 2.81 hours. The rabbit is then injected with fibrinogen labeled with $I^{125}$. After 5 hours, the animal was sacrificed and the radioactive fibrinogen accumulated in the damaged jugular vein was determined. The radioactivity on the contra-lateral (undamaged) jugular vein was also determined to serve as a control. Concurrently, another rabbit had experienced the same procedure, but received only a standard sodium chloride solution as a control. The rabbit from the normal saline solution has seven times as much radioactivity as his counterpart infused with sodium bisulfite. It is concluded that sodium bisulfite shows a definite positive effect of decreasing thrombus formation in the jugular vein.

A second rabbit, similarly evaluated along with a control rabbit displays similar results. Other rabbits similarly evaluated, died before the experiment was completed, apparently because of overdose from using this active agent.

EXAMPLE VI

A variety of agents were coded and evaluated under a code designation. Among these compounds, thiouracil, mercaptosuccinic acid, thiosemicarbazide, phenothiazine and sodium thiosulfate were included to compare sodium bisulfite to certain compounds shown in Renoux et al U.S. Pat. No. 4,148,855.

TABLE V

EFFECTS OF CODED AGENTS (0.5 mg/ml)

| L.C. LAB | UNKNOWN REAGENTS (code designation) | No. (replications) | PT (sec) | No. (replications) | PTT (sec) | Agent Identification (Decoded) |
|---|---|---|---|---|---|---|
| | CONTROL | 5 | 12.92 | 5 | 43.38 | |
| | $A_2$ | 5 | 14.60 | 5 | 48.70 | Mercaptosuccinic acid |
| | $A_3$ | 4 | 14.95 | 3 | 53.00 | Dihydroxymalic acid 2 $H_2O$ |
| | $SO_2$ | 5 | 14.94 | 5 | 49.22 | Sodium formaldehyde sulfoxaiate |
| | $SO_3$ | 5 | 19.50 | 5 | 58.60 | Sodium formaldehyde bisulfite |
| | $SO_4$ | 5 | 14.02 | 5 | 49.60 | Sodium diethyl dithiocarbamate |
| | $SI_1$ | 5 | 19.34 | 5 | 83.84 | Potassium metabisulfite |
| | $SI_2$ | 5 | 16.14 | 5 | 64.62 | Sodium sulfite |
| | $SI_4$ | 5 | 23.06 | 5 | 114.80 | Sodium bisulfite |
| | CONTROL | 2 | 13.3 | 2 | 44.3 | |
| | $A_4$ | 2 | 12.70 | 2 | 51.8 | L-Ascorbic acid |
| | $N_1$ | 2 | 13.1 | 2 | 47.5 | D-(−) Ascorbic acid |
| | $N_2$ | 2 | 12.8 | 2 | 45.4 | Thiouracil |
| | $N_3$ | 2 | 12.7 | 2 | 43.9 | Carbohydrazide |
| | $N_4$ | 2 | 13.0 | 2 | 47.6 | Thiosemicarbazide |
| | $SO_1$ | 2 | 12.9 | 2 | 45.4 | Sodium p-toluene sulfinate |
| | $SI_3$ | 2 | 13.6 | 2 | 43.0 | Sodium phosphate |
| | $SI_5$ | 2 | 13.4 | 2 | 44.2 | Sodium hypophosphite |
| | $SI_6$ | 2 | 13.5 | 2 | 42.4 | Sodium thiosulfite |

TABLE VI

EFFECTS OF VARIOUS AGENTS (0.5 mg/ml)

| Reagents | No. Exp. (Replications) | PT (sec) | No. Exp. (Replications) | PTT (sec) |
|---|---|---|---|---|
| Control | 5 | 13.40 | 4 | 42.6 |
| $Na_2S_2O_5$ | 5 | 19.56 | 4 | 77.75 |
| $NaHSO_3$ | 5 | 22.42 | 4 | 120.35 |
| Na Sulfide | 5 | 21.12 | 4 | 78.50 |
| $Na_2SO_3$ | 5 | 16.38 | 4 | 66.53 |
| $(NH_4)_2SO_3$ | 5 | 16.08 | 4 | 58.80 |
| Na—formaldehyde - $HSO_3$ | 5 | 19.68 | 3 | 56.30 |
| $K_2S_2O_5$ | 5 | 18.76 | 4 | 80.60 |
| Control | — | 13.40 | — | 42.10 |
| Na—phosphite | 1 | 12.9 | — | — |
| Na—hydrosulfite | 2 | 14.4 | — | 45.2 (39.0) |
| mecaptosuccinic acid | 1 | 14.7 | 1 | 52.6 |
| Na—thiosulfate | 1 | 13.5 | 1 | 46.2 |
| $Na_2SO_4$ | 1 | 13.6 | 1 | 44.2 |
| Na—diethylthiocarbonate | 1 | 13.6 | 1 | 48.1 |
| Na—Hypophosphite | 1 | 13.9 | 1 | 47.19 (53.8) |
| Na—formaldehyde Sulfoxalate | 1 | 13.8 | 1 | 45.1 (53.8) |

TABLE VII

FIVE 250 g RATS FED BAIT CONTAINING 0.5% SODIUM BISULFITE

| DAYS | RAT 1 g bait eaten | RAT 2 g bait eaten | RAT 3 g bait eaten | RAT 4 g bait eaten | RAT 5 g bait eaten |
|---|---|---|---|---|---|
| 1 day | 27.8 | 25.9 | 26.7 | 28.0 | 27.0 |
| 2 days | DIED | 27.9 | 17.3 | DIED | 8.0 |
| 3 days | | 19.2 | 19.4 | | 11.4 |
| 4 days | | 18.9 | 10.1 | | 10.4 |
| 9 days | | 26.8 | 27.8 | | 25.7 |
| 10 days | | 22.7 | 26.2 | | 26.3 |
| 11 days | | 23.8 | 21.0 | | 22.8 |

| FIRST DAY BLOOD FACTOR | RAT 1 | | RAT 2 | | RAT 3 | | RAT 4 | | RAT 5 | |
|---|---|---|---|---|---|---|---|---|---|---|
| | PT | PTT | PT | PTT | PT | PTT | PT | PTT | PT | PTT |
| | 26% increase | 150 | 24% increase | 150 | 28% increase | 150 | — | — | 27 | 70 |

After the determination of PT and PTT values, the coded compounds were decoded. The bisulfite and sulfites showed an in vitro effect and only one other compound (sodium formaldehyde bisulfite) was effective in increasing PT and PTT values.

The results are shown in Table V where means values of 5 replications in each case are reported. The findings demonstrate the reliability of the test method. This procedure was repeated with some additional compounds on two different days using a different control on each day. The results are shown in Table VI supra. These data indicate that the active moieties are probably the bisulfite and sulfite group.

EXAMPLE VII

Five rats, each in a separate cage, were given a bait containing 0.5 percent by weight of sodium bisulfite. The bait consisted of cracked grains (wheat, corn, millet, and corn meal). The amounts of bait eaten are summarized for an eleven day period. The first day determination of PT showed that three of the rats had an increase of PT values with no apparent change in PTT.

To evaluate the effect of sodium bisulfite in human use (this agent being known to be safe for human consumption), certain patients received this agent. The case history and observations are summarized individually below.

In each case, each patient is provided with such a bottle of Solution D, unless otherwise noted, and is instructed to dose himself (or herself, as the case may be) from the bottle so provided at the rate of seven drops to be taken orally with each of his (her) three daily meals. When the contents of one such bottle is thus so gradually consumed by an individual patient, another is provided to him (her).

CASE I

A man now age 33, height 5'10", weight 88.8 kgs., had a myocardial infarction at the age of 29, and he had been treated with heparin as an anticoagulant and also with vasodilator agents. It was felt that he had coronary atherosclerosis and hypertension. He was also on a special low salt, low fat diet.

This man improved symptomatically in the patient's estimation after about 2 weeks of treatment with Solution D. A gradual lowering of his heparin dose was achieved, and also of his vasodilator medicines. With continuance of the treatment, this man has been enjoying good health for about 3 years. It is reported that after an initial period of use of Solution D as described, this man's dosage rate was increased to 8 drops taken three times a day.

CASE II

A woman, now age 64, height 5'5", weight 86.3 kgs., had a long history of severe varicose veins in her legs, and the right leg had become so swollen that she could scarcely walk.

After about 1 month of treatment with Solution D, the swollen leg returned to normal, and her varicose condition improved as demonstrated by reduced size of the varices. After about 4 years of continuous use of Solution D, no recurrence of her original condition has resulted.

CASE III

A man, age 72 at death, height 6', weight 86.4 kgs., suffered an injury to his leg complicated by an embolus, which apparently had its inception in the leg, moved to the brain, and paralyzed the right side of his body. Subsequently he began to have thrombophlebitis in both his legs.

After use of Solution D was started, his phlebitis gradually disappeared. However, his paralysis did not regress; he continued to be bed ridden. It is reported that after an initial period of use of Solution D as described, his dosage rate was increased to 9 drops taken three times a day. After almost three years of continuously using Solution D, he had not experienced any return of phlebitis to his legs. However, this man died from a kidney infection.

CASE IV

A man, now age 79, height 5'11", weight 82 kgs., had mild hypertension, mild arthritis, mild arrhythmia, hemorrhoids, dispepsia, cyanotic fingers and toes, mild diabetes, general malaise, and lassitude. After his gall bladder had been removed at age 66, his digestion deteriorated. His diabetes was acquired shortly before treatment with sodium bisulfite began and has been controlled continuously since with Diabinese (500 mg daily).

After oral ingestion of aqueous solutions of sodium bisulfite of various concentrations (Solutions A, B, C, or D) at dose rates varying from 7 to 20 drops per meal, all of the above identified conditions improved (except for diabetes) within 2–3 months. Thereafter, they gradually disappeared and never recurred. After about seven years of continuous experimental use, the man remains in good health, and is alert and vigorous with excellent color.

After about 3–4 years of use, the man found that he had a prolonged blood clotting time whereupon he reduced his dosage rate somewhat to about 8 drops per meal per day of Solution D and his blood clotting time then normalized.

Samples of about 4 cc each of his blood were prepared. To each of these was added about 10 drops of a solution 10 weight percent and sodium bisulfite in distilled water. Each sample was then sealed into a glass vial. After about $2\frac{1}{2}$ years of storage at ambient temperatures, these blood samples have not coagulated.

At the time when prolonged clotting time was observed, the man was orally taking about 7 to 10 drops per meal per day of Solution E and his clotting time was estimated to have increased from about 5–9 to 10 minutes to 20 minutes.

This same man also, before taking this medication, had a blood cholesterol value which oscillated between 200 and 220 mg %. After about 5 years of taking this medication as described above, this man was found to have a blood cholesterol value of about 144 mg %, which value this man continues to keep through continued treatment by sodium bisulfite solutions as described above.

CASE V

A man reported to be of average weight, had been in an automobile accident about 20 years previously, as a result of which his pelvis was broken and his legs were broken in many places. Then and now, the man smokes cigarettes heavily. Over a year after the accident, when the man had slowly begun to regain use of his legs without crutches, clotting problems in his leg veins developed. The main vein in his left leg was replaced with a plastic vein which his body rejected. A second plastic vein was implanted and later blood clotting rendered it useless. A third plastic vein was implanted which has been effective for many years down to the present time. His sciatic nerve was damaged during the third vein implant operation. However, his left leg gradually became difficult to use and displayed severe swelling and poresis. His right leg also had some swelling problems.

Seven years after this third plastic vein had been in place, use of Solution C was started at a rate believed to be about 7 drops with each of three daily meals. Gradually, swelling was reduced to normal in both legs and the paresis disappeared.

After preliminary treatment with Solution C, Solution D is reported to have been substituted for Solution C at about the dose rate (7 drops with each of three daily meals). Physiotherapy is being used. Use of Solution C has not improved or changed the damage to his sciatic nerve, but walking has become easier.

I claim:

1. A method for treating a thrombotic condition in a mammal comprising administering to said mammal an antithrombotically effective amount of at least one pharmaceutically acceptable agent selected from the group consisting of alkali metals, alkaline earth metals, and ammonium salts of sulfites and bisulfites and mixtures thereof.

2. A method for treating a thrombotic condition comprising the step of orally feeding to a patient having a thrombotic condition from about 1 to 100 mg per kg of body weight per day in at least two spaced doses at least one pharmaceutically acceptable agent selected from the group consisting of alkali metal, alkaline earth metal, and ammonium salts of sulfites and bisulfites and mixtures thereof.

3. The process of claim 2 wherein after said feeding has started, said dose rate is adjusted to a value which is sufficient to cause a desired degree of change in at least one coagulation factor of such patient's blood.

4. The process of claim 3 wherein said adjusting is periodically performed.

5. The process of claim 1 wherein said agent is sodium bisulfite.

6. The method of claim 2 wherein said agent is in the form of an aqueous solution.

7. The method of claim 2 wherein said agent is orally fed to a patient at a dose rate of from about 4 to 50 mg per kg of body weight per day in at least two spaced doses.

8. The method of claim 1 wherein said thrombotic condition is demonstrated by the presence of an existing thrombus in such mammal.

9. The method of claim 1 wherein said thrombotic condition is demonstrated by the existence of an incipient thrombotic condition in such mammal.

10. The method of claim 3 wherein the dose rate is adjusted to a value which is sufficient to disrupt platelet function, coagulation factors, or both, to achieve the desired antithrombic effect.

11. The method of claim 5, wherein said sodium bisulfite is orally fed in a dose form selected from the group consisting of capsules and tablets.

12. A method for treating a thrombotic condition comprising the steps of injecting into a patient having a thrombotic condition at a dose rate of from about 1 to 100 mg per kg of body weight per day in at least two spaced doses at least one pharmaceutically acceptable agent selected from the group consisting of alkali metal, alkaline earth metal, and ammonium salts of sulfites and bisulfites and mixtures thereof.

13. The method of claim 12 wherein after said injecting has started said dose rate is adjusted to a value which is sufficient to cause a desired degree of change in at least one coagulation factor of such patient's blood.

14. The method of claim 12 wherein said agent is in the form of an aqueous solution.

15. The method of claim 13 wherein said adjusting is periodically performed.

16. The method of claim 13 wherein the dose rate is adjusted to a value which is sufficient to disrupt platelet function, coagulation factors, or both, to achieve the desired antithrombic effect.

17. A method for preventing thrombosis of deep veins following surgery in a human patient comprising the step of treating said human patient post-operatively with an antithrombotically effective amount of at least one pharmaceutically acceptable agent selected from the group consisting of alkali metals, alkaline earth metals, ammonium salts of sulfites and bisulfites and mixtures thereof as a prophylaxis.

18. A method of inhibiting one of mammalian blood coagulation factors VII, IX, X, XI and XII, said method comprising adding to a mammalian fluid selected from the group consisting of blood and blood plasma an anticoagulantly effective amount of at least one pharmaceutically acceptable agent selected from the group consisting of alkali metals, alkaline earth metals, and ammonium salts of sulfites and bisulfites and mixtures thereof.

19. A method of prolonging both the prothrombin time (PT) and partial thromboplastin time (PTT) of the blood or blood plasma of a mammal in need of such therapy, said method comprising orally administering to said mammal an anticoagulantly effective amount of at least one pharmaceutically acceptable agent selected from the group consisting of alkali metals, alkaline earth metals, and ammonium salts of sulfites and bisulfites and mixtures thereof and continuing said oral administration until the prothrombin time (PT) and thromboplastin time (PTT) are both prolonged as compared with PT and PTT values of the mammal's blood or blood plasma measured prior to initiating said therapy.

* * * * *